(12) United States Patent
Leanna et al.

(10) Patent No.: US 8,834,550 B2
(45) Date of Patent: Sep. 16, 2014

(54) APPARATUS AND METHOD FOR LOADING AND DELIVERING A STENT USING A SUTURE RETAINING MECHANISM

(75) Inventors: Gary J. Leanna, Holden, MA (US); Mark D. Wood, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1536 days.

(21) Appl. No.: 11/437,459

(22) Filed: May 19, 2006

(65) Prior Publication Data
US 2007/0270931 A1    Nov. 22, 2007

(51) Int. Cl.
*A61F 2/84* (2006.01)

(52) U.S. Cl.
USPC ........................................ 623/1.11; 606/108

(58) Field of Classification Search
USPC ............... 623/1.11, 1.23, 1.12; 606/108, 194, 606/192, 198
See application file for complete search history.

(56) References Cited

U.S. PATENT DOCUMENTS

| | | |
|---|---|---|
| 5,676,671 A | 10/1997 | Inoue |
| 5,749,921 A | 5/1998 | Lenker et al. |
| 5,776,142 A * | 7/1998 | Gunderson .................. 623/1.11 |
| 6,645,239 B1 * | 11/2003 | Park et al. .................... 623/1.11 |
| 6,669,716 B1 * | 12/2003 | Gilson et al. ................. 623/1.11 |
| 6,702,845 B1 | 3/2004 | Cully et al. |
| 6,761,733 B2 * | 7/2004 | Chobotov et al. ........... 623/1.12 |
| 6,776,791 B1 * | 8/2004 | Stallings et al. ............. 623/1.11 |
| 7,419,501 B2 * | 9/2008 | Chiu et al. ................... 623/1.12 |
| 8,535,368 B2 * | 9/2013 | Headley et al. .............. 623/1.12 |
| 2002/0151953 A1 * | 10/2002 | Chobotov et al. ........... 623/1.11 |
| 2003/0225445 A1 * | 12/2003 | Derus et al. .................. 623/1.11 |
| 2006/0025802 A1 * | 2/2006 | Sowers ........................ 606/200 |
| 2006/0167537 A1 * | 7/2006 | Larsson et al. ............... 623/1.13 |
| 2006/0282150 A1 * | 12/2006 | Olson et al. .................. 623/1.11 |

FOREIGN PATENT DOCUMENTS

| | | |
|---|---|---|
| EP | 1621149 | 2/2006 |
| WO | 9321830 | 11/1993 |
| WO | 0112256 | 2/2001 |

* cited by examiner

*Primary Examiner* — Thomas McEvoy
*Assistant Examiner* — Julie A Szpira
(74) *Attorney, Agent, or Firm* — Vidas, Arrett & Steinkraus

(57) ABSTRACT

An assembly for delivering an intraluminary member into a body lumen including a delivery catheter including an elongated tubular member, an elongated rod disposed within and slidingly engaged with the tubular member, a handle fixed to a proximal end of the rod, and at least one securing mechanism located on the handle, and a thread-like member removably secured to one end of the intraluminary member, the thread-like member extending between the intraluminary member and the handle, the at least one securing mechanism adapted to secure the thread-like member.

10 Claims, 5 Drawing Sheets

APPARATUS AND METHOD FOR LOADING AND DELIVERING A STENT USING A SUTURE RETAINING MECHANISM

FIELD OF THE INVENTION

This invention relates to a method and system for transporting, loading and delivering a stent, as well as to stent delivery assemblies. More particularly, this invention relates to the use of a suture or thread-like member to load a stent into a delivery catheter.

BACKGROUND OF THE INVENTION

An intraluminary prosthesis is a medical device used in the treatment of diseased bodily lumens. One type of intraluminary prosthesis used in the repair and/or treatment of diseases in various body vessels is a stent. A stent is generally a longitudinal tubular device formed of biocompatible material which is useful to open and support various lumens in the body. For example, stents may be used in the bodily vessel, such as in the coronary or peripheral vasculature, esophagus, trachea, bronchi colon, biliary tract, urinary tract, prostate, brain, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminary catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminary vascular stents, have included helically wound coils which may have undulations or zig-zags therein, slotted stents, ring stents, braided stents and open mesh filament/wire stents, to name a few. Super-elastic materials and metallic shape memory materials have also been used to form stents.

Although stent delivery systems are well-known in the art, the assembly of such delivery systems is often complicated. Additionally, contemporary Endoscopy practitioners increasingly use plastic self-expanding stents. Unlike most metallic self-expanding stents, the plastic ones have a tendency to permanently deform or lose some of their ability to self-expand when stored in a compressed state for a prolonged period of time. These stents are therefore preferably loaded into the stent delivery system shortly before being implanted in a patient. However, such loading often involves numerous steps and requires the use of multiple components (e.g., tools and fixtures) that are not part of the stent delivery system. Also, even with these added devices, the physician or user is often required to finish the loading process by pushing the stent into the delivery system by hand. Loading a stent in this way is therefore often difficult, time-consuming and has the potential to damage the stent. Accordingly, there is a need for simplified methods of on-site loading of a stent into stent delivery systems, while minimizing the risk of damaging the stent in the process.

SUMMARY OF THE INVENTION

The present invention is directed to a method and system for delivering a self-expanding stent into a body lumen. In particular, the present invention relates to an assembly and a method for protecting, loading and delivering a stent in combination with a stent delivery catheter, as well as to overall stent delivery systems.

In one aspect of the present invention an assembly for delivering an intraluminary member into a body lumen includes a delivery catheter and a thread-like member removably secured to one end of the intraluminary member. The delivery catheter includes an elongated tubular member, an elongated rod disposed within and slidingly engaged with the tubular member, a handle fixed to a proximal end of the rod, and at least one securing mechanism located on the handle. The thread-like member extendes between the intraluminary member and the handle. The at least one securing mechanism is adapted to secure the thread-like member. Also, the at least one securing mechanism can include at least one screw member engageable with the handle for removably securing the thread-like member thereto. The securing mechanism can include a cap removably secured to a radial protrusion on the handle. The proximal end of the handle can include a longitudinal protrusion adapted to alternatively removably secure the cap. The inner rod can include a first inner rod passage extending the length of the inner rod. The first inner rod passage communicates with a first handle passage extending the length of the handle. Also, the handle can include a second handle passage traversing at least a portion of the handle, and the thread can extend through at least a portion of the second handle passage. Further, the thread can extend through at least a portion of the inner rod passage and/or the inner handle passage.

In another aspect of the present invention a method for delivering an intraluminary stent into a body lumen includes providing a delivery catheter. The delivery catheter including an elongate inner member, an elongate outer member and a handle. Also, at least a portion of the inner member passes through and is moveably engaged with a longitudinal passage in the outer member. The handle is secured to a proximal end of the inner member and includes at least one retaining mechanism. The method also includes the steps of providing a coupling member and securing the coupling member between the intraluminary stent and the at least one retaining mechanism. At least a portion of the coupling member is disposed within the elongate outer member. The method further includes the steps of moving the outer member relative to the proximal member to cause the intraluminary stent to move into at least a portion of the longitudinal passage. The at least one retaining mechanism can include at least one screw member engageable with the handle for removably securing the coupling member thereto. Also, the retaining mechanism can include a cap adapted to engage a radial protrusion of the handle. The proximal end of the handle can include a longitudinal protrusion adapted to alternatively removably secure the cap. The inner member can include a first rod passage extending inside the length of the inner member, the first rod passage communicating with a first handle passage extending inside the length of at least a portion of the handle. The handle can also include a second handle passage traversing at least a portion of the handle, with the coupling member extending through at least a portion of the second handle passage. Further, the coupling member can extend through at least a portion of the first rod passage and/or the first handle passage. Additionally, the method can include the further steps of releasing the coupling member from the at least one retaining mechanism, removing the coupling member from the intraluminary stent, and delivering the intraluminary stent into a body lumen. Alternatively, the method can include the steps of delivering the intraluminary stent into a body lumen, moving the coupling member in the proximal direction thereby adjusting the position of the intraluminary stent, and removing the coupling member from the intraluminary stent.

These and other objectives, features, and advantages of this invention will become apparent from the following detailed description of illustrative embodiments thereof, which is to be read in connection with the accompanying drawings.

DETAILED DESCRIPTION OF THE INVENTION

The present invention relates to an assembly and method for transporting and deploying a stent, or other intraluminary member as described herein, in a bodily passageway. The assembly is suited for medical applications (particularly, endoscopic therapy) in the gastrointestinal tract, the biliary tract, the urinary tract, and the respiratory tract. In particular, a preferred embodiment of the present invention is directed to an assembly and method for transporting, loading and delivering a self-expanding esophageal stent. The system allows the clinician or user to easily load a stent into a delivery system with minimal effort and without damaging the stent. However, an assembly in accordance with the present invention could also be used in the neurological system (e.g., in the brain) and in the cardiovascular system (e.g., in the heart). Reference to bodily passageways may be to passageways in any of the aforementioned tracts and systems or elsewhere in the body.

It should be noted that references herein to the term "distal" are to a direction away from an operator of the subject invention, while references to the term "proximal" are to a direction towards the operator of the subject invention. Accordingly, when the terms "distal" and "proximal" are used herein in the context of an assembly device that is being deployed within a body, such as a human body, by an operator the term "distal" refers to a location within the body that is further within the body than a location that is "proximal" to the operator.

Figure 1:
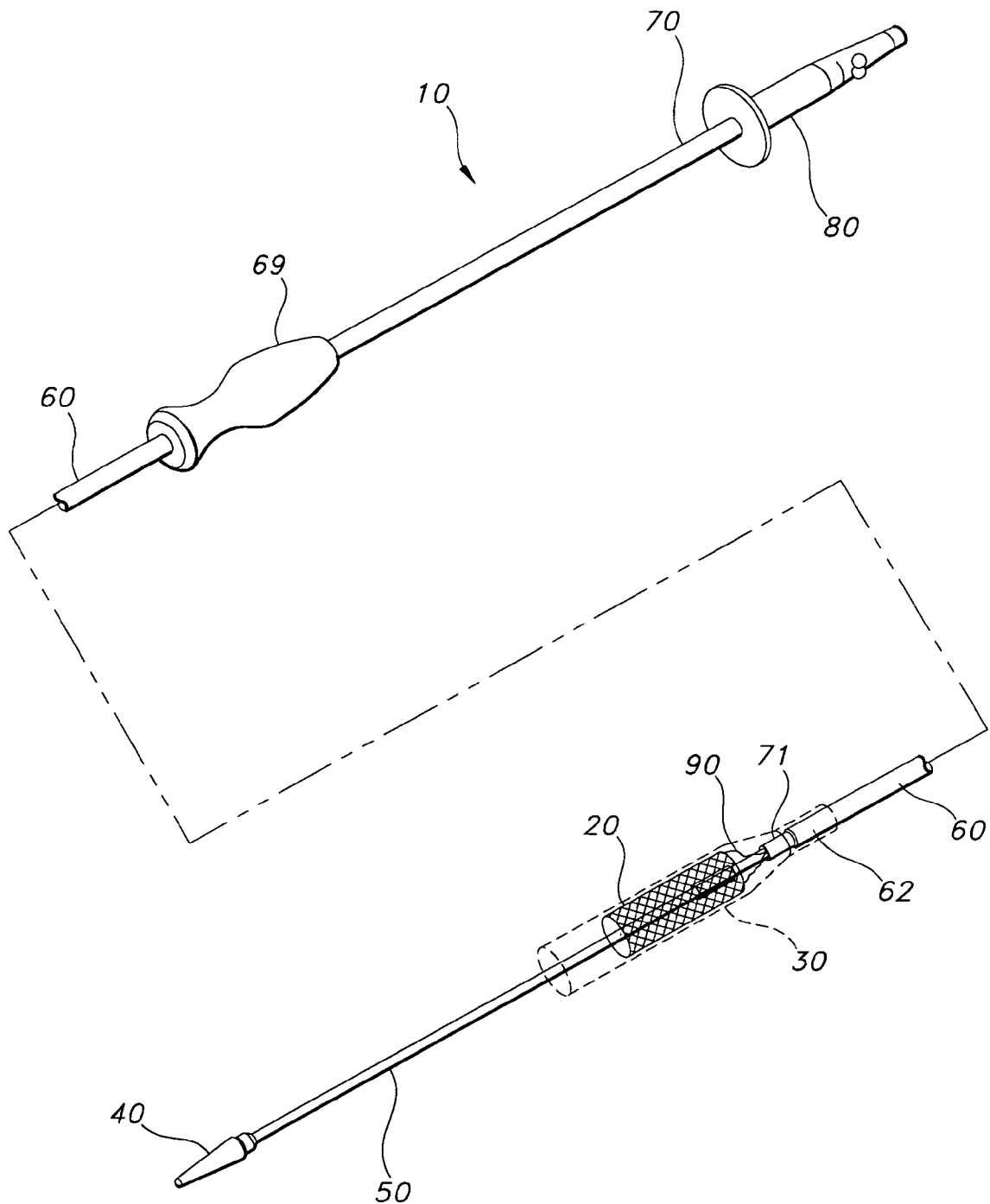
FIG. 1 illustrates a perspective view of an embodiment of a stent transfer and delivery system in accordance with the subject invention.

With reference to the drawings, FIG. 1 shows a perspective view of the stent delivery system 10 in accordance with a preferred embodiment of the subject invention. As seen in FIG. 1, a stent 20 is loaded within a stent transfer member 30 which is preferably attached to a stent delivery catheter subassembly. The stent delivery catheter subassembly preferably comprises a distal tip 40, a distal inner member 50, an outer tubular member 60, a distal handle 69, a proximal inner member 70, and a proximal handle 80. An additional feature of the preferred assembly is the loading suture 90, which is removeably coupled to the stent 20 and extends through the stent delivery catheter subassembly to the proximal handle 80.

While the present invention can be applied to the delivery of many intraluminary devices, it is particularly suited for delivering a self-expanding stent 20. A preferred stent 20 should be capable of being radially compressed and longitudinally extended for implantation into a bodily lumen. The degree of elongation depends upon the structure and materials of the stent, and may be quite varied. The diameter of the stent also may become several times smaller as it elongates. It is preferred that the stent 20 be constructed to self-expand when released from a radially compressed state. Any stent that is capable of radial expansion is preferably used in accordance with the present invention. Further, the stent 20 may be repositionable, removable and/or reconstrainable, and/or may include multiple interconnected or non-interconnected stents. Thus, various stent types and stent constructions may be employed in the invention, and the invention can be constructed to accommodate stents of various sizes and configurations.

One embodiment applies the method and system of the present invention to a braided stent 20. As used herein the term braiding and its variants refer to the diagonal intersection of elongate filaments, such as elongate wires, so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern. The passing of the filaments under and over one and the other results in slidable filament crossings that are not interlooped or otherwise mechanically engaged or constrained.

While the stent 20 can be formed of metals, plastics or other materials, it is preferred that a biocompatible construction is employed. Useful biocompatible materials include but are not limited to biocompatible metals, biocompatible alloys, biocompatible polymeric materials, including synthetic biocompatible polymeric materials and bioabsorbable or biodegradable polymeric materials, materials made from or derived from natural sources and combinations thereof. Useful biocompatible metals or alloys include, but not limited to, nitinol, stainless steel, cobalt-based alloy such as Elgiloy, platinum, gold, titanium, tantalum, niobium, polymeric materials and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonlimiting examples of bioabsorbable or biodegradable polymeric materials include poly(L-lactide) (PLLA), poly(D, L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Further, the stent 20 may include materials made from or derived from natural sources, such as, but not limited to collagen, elastin, glycosaminoglycan, fibronectin and laminin, keratin, alginate, combinations thereof and the like.

Further, the stent 20 may be made from polymeric materials which may also include radiopaque materials, such as metallic-based powders or ceramic-based powders, particulates or pastes which may be incorporated into the polymeric material. For example, the radiopaque material may be blended with the polymer composition from which the polymeric filament is formed, and subsequently fashioned into the stent as described herein. Alternatively, the radiopaque material may be applied to the surface of the metal or polymer stent. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent 20 may be selectively made radiopaque at desired areas along the stent 20 or made be fully radiopaque, depending on the desired end-product and application. Further, portions of the stent 20, for example stent filaments, may have an inner core of tantalum, gold, platinum, iridium or combination of thereof and an outer member or layer of nitinol to provide a composite filament for improved radiocapicity or visibility. Alternatively, the stent 20 may also have improved external imaging under magnetic resonance imaging (MRI) and/or ultrasonic visualization techniques. MRI is produced by complex interactions of magnetic and radio frequency fields. Materials for enhancing MRI visibility include, but are not limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 20 of the present invention may include ultrasound resonant material, such as but not limited to gold. Other features, which may be included with the stent 20 of the present invention, include radiopaque markers; surface modification for ultrasound, cell growth or therapeutic agent delivery; varying stiffness of the stent or stent components; varying geometry, such as tapering, flaring, bifurcation and the like; varying material; varying geometry of stent components, for example tapered stent filaments; and the like.

Also, as is known in the art, the materials of the stent 20 as the component filaments of the stent 20 can be further enhanced with coverings, films, coatings, and other materials and techniques. A covering may be in the form of a tubular structure, for example composed of polymeric material and/or silicone. The covering may also comprise any plastic or polymeric material, desirably a somewhat hard but flexible plastic or polymeric material. The covering may be transparent or translucent, desirably substantially or partially transparent. Furthermore, the covering may be constructed of any suitable biocompatible materials, such as, but not limited to, polymers and polymeric materials, including fillers such as metals, carbon fibers, glass fibers or ceramics. Useful covering materials include, but are not limited, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. The coating or coatings may be on the stent 20, components of the stent 20, and combinations thereof. The stent components, in part or in total, may be temporary, for example bioabsorbable, biodegradable, and the like, or may be permanent (i.e., not substantially bioabsorbable or biodegradable), for example the above-described biocompatible metals, alloys and polymers.

Further, the stent may be treated with any of the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

The stent transfer member 30 is preferably intended to protect a stent 20 or other similar inter-luminary device, before and during the time it is loaded into a delivery catheter lumen. Also, the stent transfer member 30 serves to safely radially compress the stent 20 for loading into a catheter lumen. In this way, the stent 20 can be loaded into the catheter lumen just prior to implantation in a patient's bodily passageway.

Figure 2:
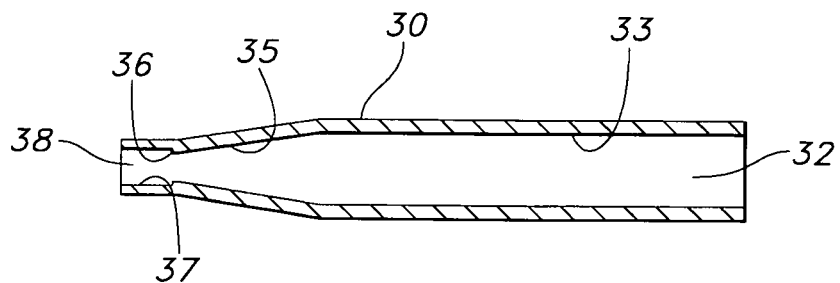
FIG. 2 illustrates a plan view of an embodiment of a stent transfer member in cross-section in accordance with the subject invention.

As shown in FIG. 2, an embodiment of the stent transfer member 30 is seen in cross-section separated from the overall delivery system 10. The stent transfer member 30 preferably has a stent holding passage 33 whose inner diameter is preferably adapted to enclose a self-expanding stent in a fully radially expanded state. Alternatively, the stent holding passage 33 could have a somewhat smaller inner circumference in order to provide an element of frictional engagement with a stent 20 loaded therein. Further, although the stent holding passage 33 preferably encloses the entire length of the stent 20, it could be longer or shorter. Thus, the holding passage 33 could be made to encircle only a portion of the stent 20. The stent transfer member 30 also preferably includes a compression funnel passage 35 which serves to radially compress a stent 20 that passes from the stent holding passage to the more proximal catheter receiving passage 37. The distal end 32 of the stent transfer member 30 is preferably open to allow unobstructed passage of the distal portions of the stent delivery catheter subassembly. The proximal end 38 of the stent transfer member 30 is preferably adapted to engage with a distal end 62 of the outer tubular member 60. Desirably, the proximal end 38 of the stent transfer member 30 has an inner cylindrical portion which acts as a catheter receiving passage 37 having a circumference that engages the outer circumference of the distal end 62 of the outer tubular member 60. A transition step 36 preferably serves as a mating seat for the outer tubular member 60. The transition step 36 is desirable to radially compress the stent 20 to the same or similar diameter as the inner lumen of the outer tubular member 60.

Alternatively, the stent transfer member 30 may include radially protruding ribs (not shown) within at least one of the transfer member passages 33, 35, 37 in order to reduce the frictional surfaces that engage with the stent 20 or outer tubular member 60. Such ribs could extend longitudinally, circumferentially, helically, or any combination thereof, within all or a portion of a passage 33, 35, 37. Such radial ribs could be limited to only a portion of one of the aforementioned passages 33, 35, 37 or included throughout. Similarly, the transfer member 30 could include porous, textured or bumpy surfaces to either increase or decrease frictional surfaces on either the inner stent engagement surfaces or outer handling surfaces.

It should be understood that the length or diameter of the stent transfer member 30 could be constructed to suit a particular application and/or stent. Also, the edges of the stent transfer member 30 could have a beveled profile. Further, the transfer member 30 could be constructed with one or more longitudinal slits or slots that can extend along the entire length or only a portion of the transfer member 30. As a further alternative, the transfer member 30 could engage the outer tubular member 60 using other known coupling techniques. Further still, as discussed above with regard to stents 20, the transfer member 30 could be coated. Such coatings could reduce or enhance frictional engagement. Additionally, such coatings could further be designed to transfer or adhere to the stent 20 after it is removed from the transfer member 30.

While the stent transfer member 30 is shown as a unitary member, it can alternatively be formed by separate elements. In this way, the stent transfer member 30 could be made to split open or have a portion that can be removed to facilitate loading the stent 20 therein. For example, the stent transfer member 30 could be split or hinged along it's longitudinally axis. However, such an embodiment would preferably provide some mechanism for holding the separate elements together. Also, although a generally cylindrical outer structure is illustrated in FIG. 2, the stent transfer member 30 could have almost any shape to its outer surfaces. Whether to provide ergonomic features, a handle, engagement surfaces for tools, or simply ease of manufacture, it should be understood that the outer surfaces of the stent transfer member 30 could be altered from that shown. With regard to the inner surfaces 33, 35, 37 a cylindrical configuration is preferred, but alternative shapes are anticipated.

Figure 3:
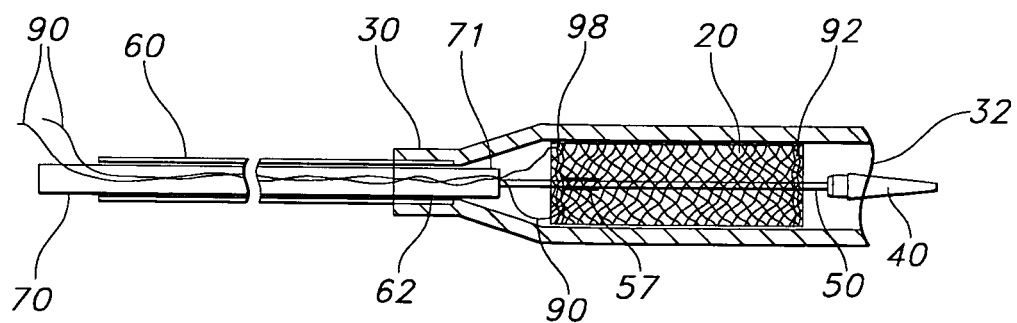
FIG. 3 illustrates an enlarged plan view of a distal portion of the assembly shown in FIG. 1, in cross-section.

With reference to FIG. 3, in accordance with the present invention a loading suture 90 or other suitable thread is preferably braided or woven into a proximal end the stent 20. The loading suture 90 can be braided or woven directly into the wires, filaments or structure of the stent 20 itself. However, it is preferable that a central portion of a loading suture 90 be woven to engage a separate retrieval suture 98 that is part of the stent 20. The loading suture 90 can be threaded through any number of loops of the proximal retrieval suture 98. The two ends of the loading suture 90 then preferably extend proximally from the stent 20 to the proximal end of the delivery system 10.

Retrieval sutures 92, 98 located at the distal and proximal ends of the stent 20 can be useful to a physician after the stent is delivered into a body lumen. Such sutures 92, 98 remain on the stent after it is implanted and allow the physician to reposition and/or remove the stent. Devices such as graspers or hooks can be used to pull on the retrieval sutures 92, 98. When pulled, the retrieval suture 92, 98 is preferably adapted to constrict the end of the stent in a purse string type movement. This constriction of an end of the stent 20 can make it easier for it to be pulled through an intraluminary passage.

It should be noted that references herein to the term "suture" denotes a length of thread, thread-like member, cord, filament, wire or other similar structure. It should be understood that sutures as referred to herein can be made of a single material or composite materials. Accordingly, the terms "suture," "thread," "cord," "filament," and/or "wire" are used interchangeably herein.

As seen in FIG. 3, once the loading suture 90 is coupled to the stent 20 and fed through the delivery catheter subassembly toward the proximal end of the assembly, the stent 20 is preferably loaded into the stent holding passage 33. This can be done before or after the stent transfer member is mounted onto the distal end 62 of the outer tubular member 60. The configuration shown in FIG. 3 maintains the stent 20 in a radially expanded state and can serve to protect the stent from the time of assembly-until the stent is loaded into the lumen of outer tubular member 60. Thus, the stent need not be compressed into a delivery catheter for an extended period, potentially causing permanent deformation.

Figure 4:
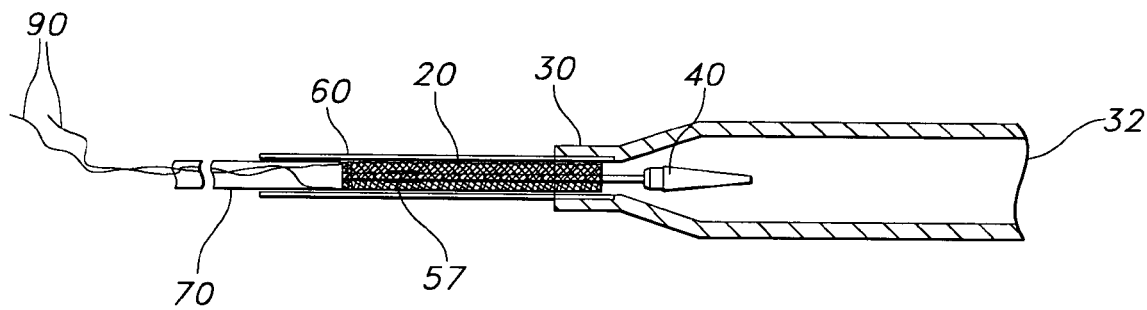
FIG. 4 illustrates an enlarged plan view of a distal portion of the assembly shown in FIG. 1, after the stent has been loaded in accordance with the subject invention.

With reference to FIGS. 3 and 4, the distal inner member 50 and the proximal inner member 70 are preferably fixed to one another, functioning as a unitary member, along with distal tip 40. These three inner members 40, 50, 70 are preferably coaxially configured within outer tubular member 60. Also, as with a more traditional delivery catheter, the outer tubular member 60 is slidable axially relative to the three inner members 40, 50, 70. Further, when the stent transfer member 30 is mounted onto the distal end 62, it preferably slides axially in conjunction with the outer tubular member 60, and thus also relative to inner members 40, 50, 70. Thus, two handles are provided for manually sliding these elements relative to one another. The distal handle 69 controls the sliding movement of the outer tubular member 60, along with, if attached, stent transfer member 30. The proximal handle 80 likewise controls the sliding movement of the above mentioned inner members 40, 50, 70. This relative sliding movement is used for both loading and deployment (delivery) of the stent 20.

The inner members 50 and 70 and outer member 60 are preferably formed of a body compatible material. Desirably, the biocompatible material is a biocompatible polymer. Examples of suitable biocompatible polymers include, but are not limited to, polypropylene (PP), polytetrafluoroethylene (PTFE), polyethylene terephthalate (PET), high density polyethylene (HDPE) and the like. Materials for the members 50, 60, 70 may be the same or different. Additionally, the outer member 60 and the stent transfer member 30 could have coverings, films, coatings, and the like, desirably a polymeric covering, disposed over the inner surfaces to aid in the loading and/or deployment of the stent 20.

The loading suture 90 preferably provides a link or coupling means between the stent 20 and the proximal end of the proximal inner member 70. In a preferred embodiment, the loading suture 90 is removeably secured to the proximal handle 80. The desired purpose of securing the loading suture 90 is to limit the relative axial movement of the stent 20 away from the proximal inner member 70 and/or the proximal handle 80. Thus, by moving the distal handle 69 away from the proximal handle 80, the stent 20 is caused to be drawn through the compression funnel passage 35 and into an inner lumen of the outer tubular member 60, as seen in FIG. 4. During this movement, the stent 20 is transferred from the stent holding passage 33 to the inner lumen of the outer tubular member 60. Also, during this movement the stent 20 is preferably made to radially compress and engage onto the distal inner member 50, or at least engage with the stent holder 57. Thus, the configuration seen in FIG. 4 shows the stent 20 fully loaded within the inner lumen of the outer tubular member 60. Alternatively, the distal end 62 of the outer tubular member 60 can include an inner bevel to aid in loading the stent 20.

In one embodiment, the loading suture 90 can simply be threaded between the outer surface of the proximal inner member 70 and the inner surface of the outer tubular member 60. Alternatively, the loading suture can be made to pass through auxiliary passage 75 in the proximal inner member 70, seen in FIG. 5. The loading suture 90 can also be made to pass through the entire length of the proximal inner member 70, the inside of the proximal handle 80 and out the proximal end of the proximal handle 80. Alternatively, an additional opening can be made in the outer surface of the proximal inner member 70, allowing the loading suture 90 to exit the auxiliary passage 75. Such a loading suture 90 exit (not shown) can be disposed on the proximal inner member 70 at a location between the distal handle 69 and proximal handle 80. Further, this alternative suture opening in the proximal inner member 70 can correspond with a stent release position discussed below.

During deployment or delivery of the stent 20, as the two handles 69, 80 are drawn toward one another, there is a particular distance between them that corresponds with release of the stent 20. As the proximal edge of the distal handle 69 slides along the surface of the proximal inner member 70, a position on the surface of the proximal inner member 70 will correspond with the position that releases the stent 20 from the outer tubular member 60. Thus, a marker for this release position can be provided on the surface of the proximal inner member 70. Alternatively, the loading suture opening could be positioned to also function as this type of marker.

Figure 5:
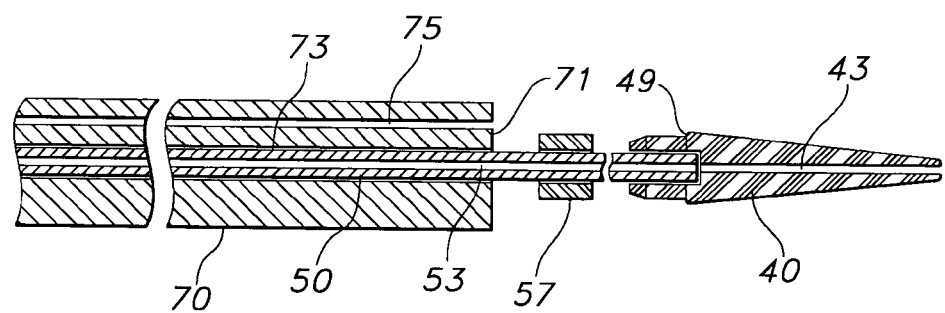
FIG. 5 illustrates an enlarged plan view of an embodiment of a distal portion of the distal subassembly in cross-section, in accordance with the subject invention.
Figure 6A:
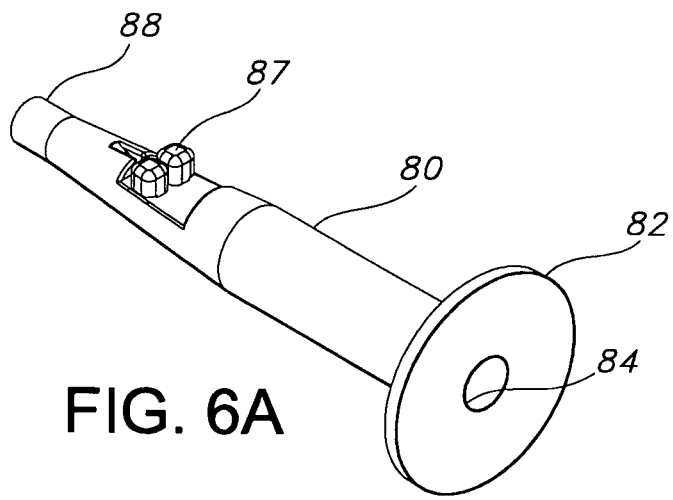
FIGS. 6A-D illustrate perspective, left side, plan and right side views, respectively, of an embodiment of the proximal handle in accordance with the subject invention.
Figure 6B:
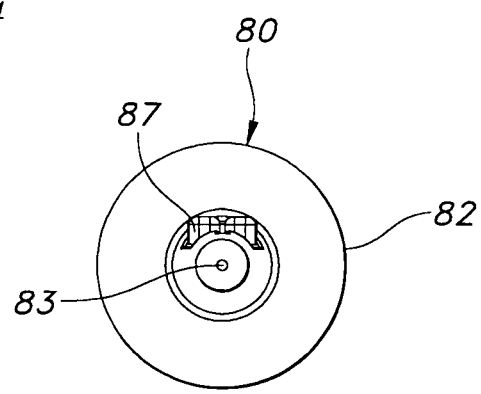
Figure 6C:
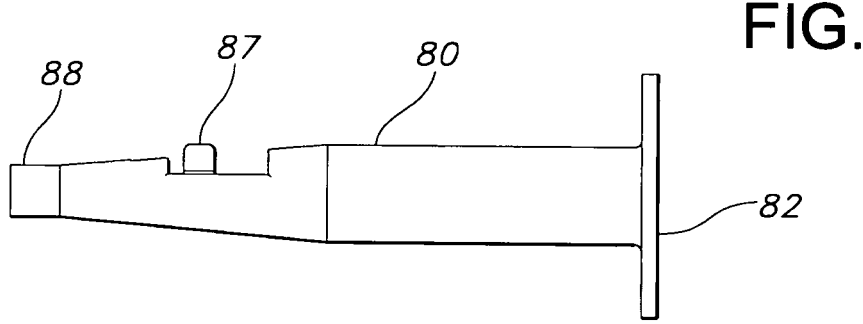
Figure 6D:
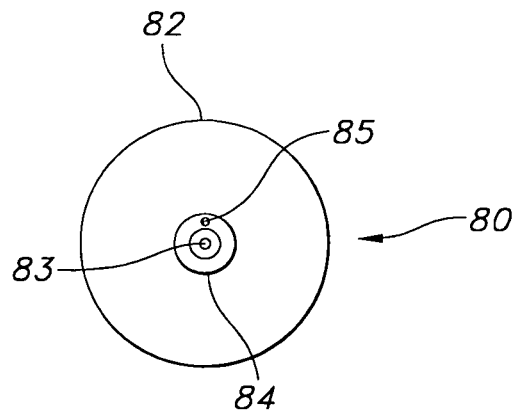

With reference to FIG. 5, the distal inner member 50 is preferably disposed and secured within an inner passage 73 in the proximal inner member 70. Similarly, the stent holder 57 and the distal tip 40 are preferably fixed to the distal inner member 50. These elements can be secured by frictional engagement or more permanent bonding. Alternatively, the distal inner member 50 and the proximal inner member 70 could be made as one unitary member. In this way, the distal subassembly seen in FIG. 5 will preferably move in unison. Also, the distal inner member 50 preferably extends through the entire length of the proximal inner member 70 and beyond it in the distal direction.

The distance between the distal end 71 of the proximal inner member 70 and the proximal end 49 of the distal tip 40 is preferably suited to accommodate the stent 20 in a radially compressed state, as seen in FIG. 4. It should be noted that as the stent 20 is radially compressed, it tends to axially expand. Thus, it is desired that the distance between the proximal inner member 70 and the distal tip 40 comfortably accommodate the axially expanded state of the stent 20. The stent holder 57 is preferably provided to enhance the frictional engagement between the stent 20 and the distal inner member 50. Once compressed onto the stent holder 57, the stent 20 will slide axially in unison with the distal inner member 50, unless the stent is radially released. Thus, as seen in FIG. 4, once compressed into the outer tubular member 60, at least a portion of the stent 20 is preferably engaged with the stent holder 57. Preferably, the stent holder 57 is made of a soft deformable or low durometer polymer that allows it to conform to the inner surface of the stent. For example, the stent holder 57 could be made from 2533 Pebax® (ARKEMA, Courbevoie, France) a hardness 25, shore D, non-plasticized flexible Polyamide or other polymers, such as Dynaflex® (GLS Corp., McHenry, Ill.). However, it is understood that other suitable materials that function to enhance engagement with the stent could be used. Additionally, although the stent holder 57 is shown as an annular band, alternatively it could extend around only a portion or separate portions of the distal inner member 50. In other words, the stent holder 57 may not have to completely encompass the distal inner member 50, but may be only partially disposed around a circumferential portion thereof. Moreover, the stent holder 57 may have a pattern, such as a surface pattern of indentations and/or protrusions for facilitating securement of the stent 20. In some embodiments, the stent holder 57 may have barbs, pins or protrusions which may engage the stent 20. Further, with any of the embodiments, the device or system may include multiple stent holders 57, either axially spaced apart or axially juxtaposed.

Once the stent 20 is loaded as seen in FIG. 4, the stent transfer member 30 and the loading suture 90 can be removed from the assembly. Thereafter, the delivery catheter subassembly that remains is preferably used to surgically deliver the stent 20, into a body lumen. In one alternative embodiment, the loading suture 90, need not be removed before delivery of the stent 20 into the patient. In this alternative embodiment, the loading suture 90 can be used to adjust the axial delivery position of the stent 20 in the proximal direction within the body lumen. In other words, the loading suture 90, is thus used to pull the stent 20 back to a more proximal location. Once positioned as desired, the loading suture 90 can be removed from the stent 20 as discussed below.

Removal of the stent transfer member 30 is preferably relatively simple. A frictional mounting between the applicable two elements 30, 62 is desirable, for easy removal. Alternatively, a screw-thread or other known means of engagement between the two elements could be provided.

With regard to the removal of the loading suture 90, at least one end the loading suture 90 is preferably detached from the proximal handle 80 or the proximal inner member 70, where it was secured. Then, by detaching and pulling the other end of the loading suture 90, it is preferably pulled out of the stent 20 and the overall assembly. The loose weaving or braiding configuration between the loading suture 90 and the retrieval suture 98, should allow the suture 20 to be removed in this way. Even if the loading suture 90 were woven into the stent 20 itself, this removal technique could still be used. Once the loading suture 90 has been removed from the stent 20 and the stent delivery catheter subassembly, it can be set aside and/or discarded. In this way, with the stent transfer member 30 and loading suture 90 removed, the stent delivery catheter subassembly is now loaded with a stent for delivery and can be inserted into a body lumen for surgical delivery.

As seen in FIGS. 6A-D, the proximal handle 80 (also referred to as a luer body) is preferably made to include a fastener, clamp or locking mechanism for retaining the loading suture 90. FIG. 6A-D show suture locks 87 which comprise two screw-like members with cylindrical or semi-spherical heads that are preferably adapted to be easily manipulated by hand, without the use of tools. Each end of the loading suture 90 can be rapped around one of these suture locks 87 and secured thereon. Alternatively, the suture lock 87 could be fully or partially unscrewed exposing the screw shaft which can be used to secure the suture. In this embodiment, once the suture is wrapped around or pinned under the screw shaft, the suture lock 87 could then be tightened down to retain the suture in position.

The proximal handle shown in FIGS. 6A-D preferably includes an auxiliary passage 85 that corresponds to auxiliary passage 75 in the proximal inner member 70. Thus, the loading suture 90 can be fed through these auxiliary passages 75, 85. The auxiliary passage 85 preferably ends either near the suture locking mechanism 87 or at the distal end 88 of the proximal handle 80. The receiving passage 84 is intended to mate with the proximal end of the proximal inner member 70. Additionally, a luer flange 82 or other similar ergonomic feature can be provided on the distal end of the proximal handle 80.

As part of an overall stent delivery system, it is preferred that an inner passage be provided for flushing fluids through the stent delivery catheter subassembly. In this way, the proximal handle 80 is preferably provided with a flush passage 83 which traverses the length of the proximal handle. This flush passage 83 is preferably open to and in communication with inner passage 53 in the distal inner member 50. Further, this inner flow passage should preferably extend all the way through to an inner passage 43 in the distal tip 40. In this way, an inner flush passage is provided from end to end in the overall assembly. Additionally, the proximal end 88 of the proximal handle 80 can be molded to receive fluid flushing attachments or other surgical instrument.

Figure 7B:
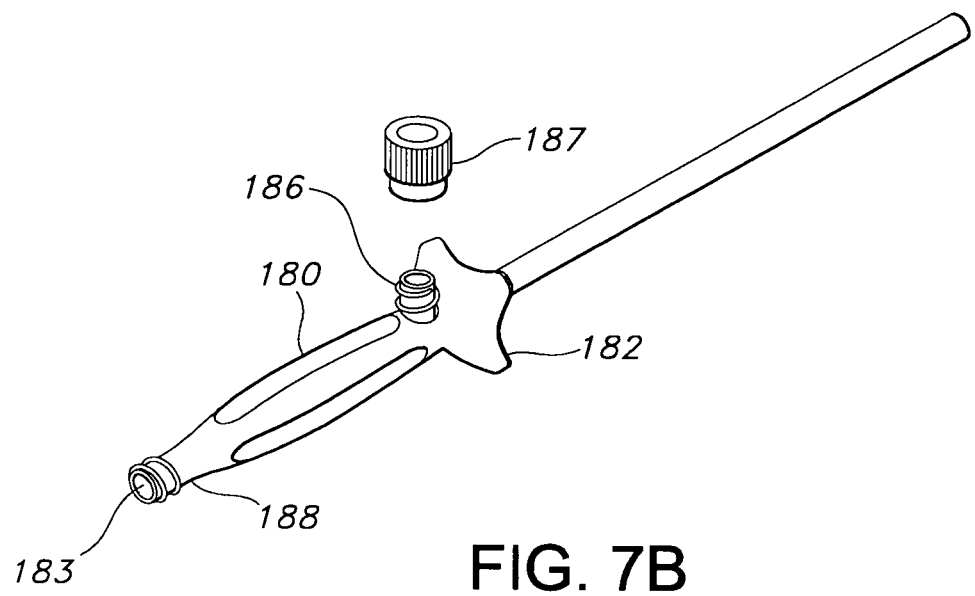
FIGS. 7A-B illustrate perspective views of another embodiment of the proximal handle in accordance with the subject invention.
Figure 7A:
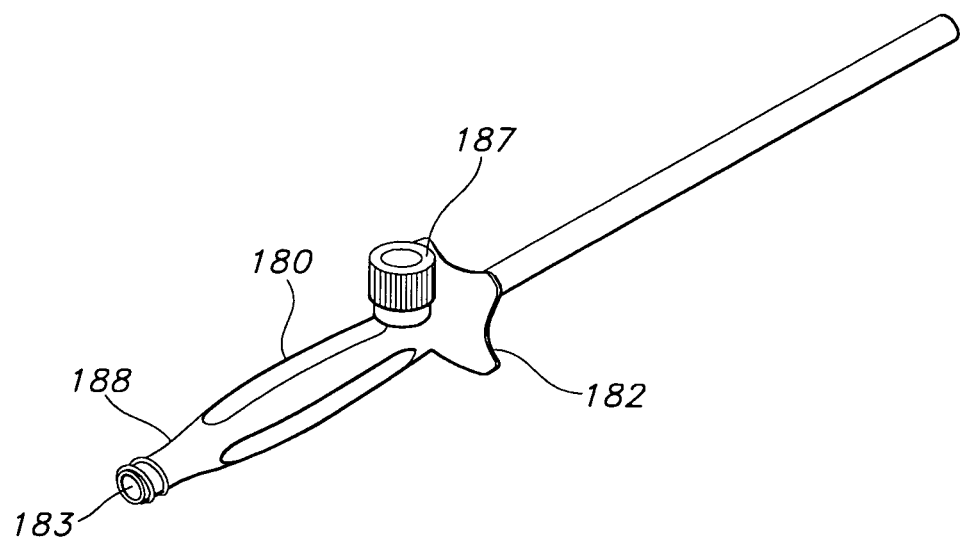

FIGS. 7A and 7B illustrate an alternate embodiment for the proximal handle 180. This embodiment demonstrates many of the same features as the proximal handle discussed above. For example, a somewhat different luer flange 182 is provided. This embodiment also preferably uses a screw-on cap 187 as a suture lock. The screw-on cap 187 is preferably adapted to be mounted on a portion of the proximal handle 180. The cap is preferably mounted onto a threaded cylindrical port 186 protruding from a lateral surface of the handle 180. Alternatively, the same screw threading can be molded onto the proximal end 188 to receive the screw-on cap 187. As a further alternative, multiple mounting locations can be provided as seen in FIGS. 7A-B. Nonetheless, the two ends of the loading suture 90 can be wrapped around either threaded cylindrical port 183, 186 before being secured by the cap 187. Additionally, the loading suture 90 can be fed through an inner passage in the port 186 or the flush passage 183, and then secured by the screw-on cap 187. As yet a further alternative, the mounting locations could engage the cap 187 with a snap lock design, rather than screw threads.

In either of the previously described embodiments of the proximal handle 80, 180, one end of the loading suture 90 can be permanently attached to one of the suture locks 87 or the screw-on cap 187. This can be done by injection molding, adhesives, heated bonding or other known techniques. It is desirable to allow the other end to be removed so that it can be pulled out of the stent 20 and the assembly 10, as discussed above. As a further alternative, both ends of the loading suture 90 could be permanently secured, thus requiring the surgeon or user to simply cut them off prior to pulling the loading suture out.

Additional features of useful stent delivery systems are further described in U.S. patent application Ser. No. 11/437,889, entitled "Apparatus and Method for Loading and Delivering a Stent", filed on same date herewith, attorney docket 792-57; and U.S. patent application Ser. No. 11/437,455, entitled "Apparatus and Method for Loading and Delivering a Stent", filed on same date herewith, attorney docket 792-36, the contents of which are incorporated herein by reference.

While various embodiments of the present invention are specifically illustrated and/or described herein, it will be appreciated that modifications and variations of the present invention may be effected by those skilled in the art without departing from the spirit and intended scope of the invention.

What is claimed is:

1. An assembly for delivering an intraluminary member into a body lumen comprising:
   a delivery catheter including:
   an elongated tubular member,
   a first inner member disposed within and slidingly engaged with the tubular member, the first inner member defining a lumen,
   a second inner member, a first portion of the second inner member disposed within and secured to the lumen of the first inner member, a second portion of the second inner member extending from a distal end of the first inner member,
   an intraluminary holder engaged to a portion of the second inner member,
   a handle fixed to a proximal end of the first inner member, and
   at least one securing mechanism located on the handle;
   a stent transfer member including an inner cylindrical portion disposed at a distal end of said elongated tubular member, said stent transfer member comprising a transition step to serve as a mating seat for said elongated tubular member;
   a radially expandable intraluminary member having a first end and a second end and defining an intraluminary member lumen therebetween, wherein the second inner member is disposed within the intraluminary member lumen;
   a retrieval suture located at the first end of the intraluminary member; and
   a thread-like member removeably secured to one end of the intraluminary member, the thread-like member removeably secured to one end of the intraluminary member, the thread-like member extending between the intraluminary member and the handle, the at least one securing mechanism adapted to secure the thread like member;
   wherein said thread-like member is removeably secured to one end of the intraluminary member such that two ends of said thread-like member extend from said intraluminary member to said handle; and
   wherein pulling said thread-like member towards said proximal end results in reducing a diameter of said intraluminary member through compression of said intraluminary member by the stent transfer member and securing the intraluminary member to the intraluminary holder.

2. The assembly of claim 1, wherein the at least one securing mechanism includes at least one screw member engageable with the handle for removeably securing the thread-like member thereto.

3. The assembly of claim 1, wherein the securing mechanism includes a cap removeably secured to a radial protrusion on the handle.

4. The assembly of claim 1, wherein the proximal end of the handle includes a longitudinal protrusion adapted to removeably secure the cap.

5. The assembly of claim 1, wherein the first inner member includes a first inner member passage extending the length of the inner rod, the first inner member passage communicating with a first handle passage extending the length of the handle.

6. The assembly of claim 5, wherein the handle includes a second handle passage traversing at least a portion of the handle, and wherein the thread-like member extend through at least a portion of the second handle passage.

7. The assembly of claim 5, wherein the thread-like member extends through at least a portion of the first inner member passage.

8. The assembly of claim 7, wherein the thread-like member extends through at least a portion of the inner handle passage.

9. The assembly of claim 1, wherein the intraluminary member is a stent.

10. The assembly of claim 1, further comprising a second retrieval suture located at the second end of the intraluminary member.

\* \* \* \* \*